US009085506B2

(12) United States Patent
Galle et al.

(10) Patent No.: US 9,085,506 B2
(45) Date of Patent: *Jul. 21, 2015

(54) PROCESS FOR PREPARING 3-AMINOMETHYL-3,5,5-TRIMETHYLCYCLOHEXYLAMINE

(75) Inventors: Markus Galle, Dortmund (DE); Gerda Grund, Coesfeld (DE); Axel Hengstermann, Senden (DE); Michael D Hinton, Theodore, AL (US); Rolf Hirsch, Marl (DE); Robert Jansen, Bottrop (DE); Cord Knoop, Haltern am See (DE); Christian Lettmann, Coesfeld (DE); Juergen Lippe, Gelsenkirchen (DE); Martin Maier, Herne (DE); Joerg-Joachim Nitz, Oberhausen (DE); Matthias Orschel, Muenster (DE); Martina Ortelt, Duelmen (DE); Norbert Richter, Marl (DE); Armin Rix, Marl (DE); Markus Schwarz, Haltern am See (DE); Guido Streukens, Wuppertal (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/991,718

(22) PCT Filed: Nov. 18, 2011

(86) PCT No.: PCT/EP2011/070442
§ 371 (c)(1),
(2), (4) Date: Jun. 5, 2013

(87) PCT Pub. No.: WO2012/076317
PCT Pub. Date: Jun. 14, 2012

(65) Prior Publication Data
US 2013/0253226 A1    Sep. 26, 2013

(30) Foreign Application Priority Data
Dec. 8, 2010   (DE) .................. 10 2010 062 603

(51) Int. Cl.
C07C 209/00 (2006.01)
C07C 209/48 (2006.01)
C07C 209/26 (2006.01)
C07C 253/10 (2006.01)
C07C 45/74 (2006.01)

(52) U.S. Cl.
CPC .............. *C07C 209/48* (2013.01); *C07C 45/74* (2013.01); *C07C 209/26* (2013.01); *C07C 253/10* (2013.01); *C07C 2101/14* (2013.01)

(58) Field of Classification Search
None
See application file for complete search history.

(56) References Cited

U.S. PATENT DOCUMENTS

| 3,337,632 | A | * | 8/1967 | Baron et al. ................. 568/350 |
| 5,055,620 | A | | 10/1991 | Schutz |
| 5,627,303 | A | * | 5/1997 | Braithwaite et al. .......... 568/388 |
| 8,536,370 | B2 | | 9/2013 | Grund et al. |
| 2009/0048466 | A1 | | 2/2009 | Lettmann et al. |
| 2010/0041921 | A1 | | 2/2010 | Lettmann et al. |

FOREIGN PATENT DOCUMENTS

| DE | 1 240 854 | 5/1967 |
| EP | 0 394 967 | 10/1990 |
| WO | 2007 093240 | 8/2007 |
| WO | 2008 107226 | 9/2008 |
| WO | 2012 076314 | 6/2012 |
| WO | 2012 076315 | 6/2012 |
| WO | 2012 171830 | 12/2012 |

OTHER PUBLICATIONS

International Search Report Issued Apr. 24, 2012 in PCT/EP11/70442 Filed Nov. 18, 2011.
U.S. Appl. No. 13/990,602, filed May 30, 2013, Orschel, et al.
U.S. Appl. No. 13/885,532, filed May 15, 2013, Lettmann, et al.
U.S. Appl. No. 14/124,449, filed Dec. 6, 2013, Schwarz, et al.
U.S. Appl. No. 14/116,233, filed Nov. 7, 2013, Orschel, et al.
U.S. Appl. No. 14/454,786, filed Aug. 8, 2014, Nitz, et al.

* cited by examiner

*Primary Examiner* — Sudhakar Katakam
(74) *Attorney, Agent, or Firm* — Oblon, McClelland, Maier & Neustadt, L.L.P.

(57) ABSTRACT

The invention relates to an improved process for preparing 3-aminomethyl-3,5,5-trimethylcyclohexylamine, referred to hereinafter as isophoronediamine or, in abbreviated form, IPDA, by: I. preparation of isophorone by catalyzed aldol condensations with acetone as reactant; II. reaction of isophorone with HCN to form isophoronenitrile (IPN, 3-cyano-3,5,5-trimethylcyclohexanone); III. catalytic hydrogenation and/or catalytic reductive amination (also referred to as aminative hydrogenation) of 3-cyano-3,5,5-trimethylcyclohexanone, hereinafter called isophoronenitrile or, in abbreviated form, IPN, to give the isophoronediamine.

65 Claims, No Drawings

PROCESS FOR PREPARING 3-AMINOMETHYL-3,5,5-TRIMETHYLCYCLOHEXYLAMINE

The invention relates to an improved process for preparing 3-aminomethyl-3,5,5-trimethylcyclohexylamine, referred to hereinafter as isophoronediamine or IPDA for short, by I. preparation of isophorone by catalyzed aldol condensations of acetone as a reactant II. reaction of isophorone with HCN to form isophoronenitrile (IPN, 3-cyano-3,5,5-trinnethylcyclohexanone);

III. catalytic hydrogenation and/or catalytic reductive amination (also referred to as aminating hydrogenation) of 3-cyano-3,5,5-trimethylcyclohexanone, referred to hereinafter as isophoronenitrile or IPN for short, to give isophoronediamine.

PRIOR ART FOR I

Isophorone is used inter alia as a high-boiling solvent in the coatings industry, printing inks industry, adhesives industry and crop protection industry. According to the known prior art, the isophorone can be processed further, for example to give isophoronenitrile, isophoronediamine, isophorone diisocyanate or ketoisophorone.

Isophorone is the trimeric condensation product of acetone. Isophorone is prepared via a catalyzed aldol condensation of acetone.

Both the existing patent literature and the scientific publications for preparing isophorone can be divided essentially into two areas. A distinction is drawn between liquid phase and gas phase processes. CN 101633610A also describes the condensation reaction for preparation of isophorone with supercritical acetone.

While mainly heterogeneous solid catalysts are employed in the gas phase processes described, both homogeneous and heterogeneous catalyst systems are used in liquid phase processes.

The reaction in the liquid phase is described in the patent literature virtually exclusively under alkaline conditions at elevated temperatures and high pressures.

In the field of isophorone chemistry, several patents to the Shell Development Company are known (U.S. Pat. No. 2,351,352, U.S. Pat. No. 2,344,226, U.S. Pat. No. 2,399,976, U.S. Pat. No. 2,419,051). U.S. Pat. No. 2,399,976 describes inter alia a condensation process for preparation of isophorone in a circulation reactor by means of alkali catalysis. In the process, the alkali used is recycled back into the reactor after phase separation, while the water of reaction formed is removed from the reactor circuit with the organic phase.

In addition, U.S. Pat. No. 2,419,051 describes a process in which hydrolysis of the higher condensation products can reverse the condensation of some of the overcondensates. The hydrolysis is performed in a pressure reactor at temperatures between 130-235° C. with an elevated alkali concentration.

In order to prevent phase separation in the synthesis, and hence to achieve a monophasic reaction regime, the applications of the Societe Industrielle Des Derivatives De L'Acetylene (DE 10 58 047, GB733650) describe alcohols as solubilizers. This process leads to a shorter reaction time. It is additionally stated there that the recycling of removed by-products into the reaction zone of the reactor enhances the selectivity of isophorone formation.

In the patent documents of Hibernia Chemie (DE 10 95 818, DE 11 44 269, DE 12 05 525, DE 11 65 018) from the 1960s, not only the use of a monophasic reactant/catalyst mixture with low alkali concentrations but also workup by means of a hydrolysis column is described. Isophorone is prepared here in a pressure reactor by condensation of acetone in the liquid phase by means of amounts of alkali (NaOH or KOH) of less than 1% as a catalyst and using amounts of water of less than 20% at temperatures of 150-250° C. The two phases which form in the reaction are emulsified both by a suitable reaction regime (reactor construction, pulse generator) and by the use of an emulsifier in order to ensure good contact between catalyst and the reactants (DE 10 95 818).

In addition, DE 12 05 525 describes the workup of by-products, called overcondensates. At 120-300° C., the hydrolysis of the overcondensates takes place with an aqueous alkali solution in what is called a pressure distillation column with constant removal of the acetone formed.

Pure isophorone is obtained from isophorone-containing condensation products by a removal of the low boilers by distillation under the same pressure at which the condensation is performed and by a further workup of the overcondensates still existing by distillation under reduced pressure (DE 11 44 269).

According to the application of BP Chemicals, use of potassium hydroxide solution (KOH) instead of the catalyst which is otherwise customary, sodium hydroxide solution (NaOH), can enhance the isophorone yield by up to 7% with constant selectivity (DE 25 20 681).

It has also been stated that the product quality of the isophorone can be increased by discharging colored substances from the reaction column in a sidestream, and purifying this stream by distillation and acidic reaction (DE 26 45 281).

There also exist applications regarding isophorone preparation from Daicel Chemical Industries (JP 8245485, JP 8245486) from the 1990s. These state that reduction of the water concentration in the reactant stream, and also recycling of the aqueous alkali phase after phase separation into the hydrolysis section of the reactive distillation, can enhance the isophorone conversion.

As well as the liquid phase processes by means of homogeneous catalyst systems mentioned so far, there is also a patent publication involving heterogeneous catalyst systems in the liquid phase.

Thus, Elf Atochem S. A. in U.S. Pat. No. 5,849,957 describes the use of hydrotalcites ($Mg_{1-x}Al_xO_{1+x}$) as a heterogeneous catalyst system for the preparation of isophorone. In batchwise stirred tank experiments, it was possible with such a catalyst to achieve an acetone conversion of 38% and a selectivity for isophorone of 51%.

The prior art frequently describes the preparation of isophorone by means of heterogeneous catalysts.

The documents of Union Carbide (U.S. Pat. No. 4,086,188, U.S. Pat. No. 4,165,339, EP 095 783) describe the preparation of isophorone by means of lithium- or zinc-doped hydrotalcite-type precipitation catalysts. These catalysts can achieve, at an acetone conversion of 24%, a selectivity of 47% for isophorone (U.S. Pat. No. 4,086,188), and the catalyst can be fully regenerated by burning off the coking residues (U.S. Pat. No. 4,165,339). By optimizing the preparation conditions, the service life of such a catalyst can be increased to up to about 1000 hours (EP 095 783).

The patents of Aristech Chemical Corporation (WO9012645, WO9507255) describe various oxidic magnesium/aluminum catalysts which are prepared by slurrying pseudoboehmite and magnesium oxide (WO 9012645). At an acetone conversion of 30%, the selectivity for isophorone is 76%.

As well as the catalysts, Aristech Chemical Company also describes a process for preparing isophorone in the gas phase in a fixed bed reactor (WO 95072559). The acetone conversion is limited here to 10-35% in order to minimize the formation of coking residues.

There is also a series of applications (JP 9059204, JP 9151152, JP 9151153, JP 9157207, JP 9157208, JP 9169687, JP 9169688) from Mitsui Toatsu Chemicals, which claim various zeolite and magnesium/alkali metal catalysts for the preparation of isophorone.

Scientific publications likewise describe, as well as the catalyst systems already mentioned in the patents, the use of carbon nanotubes as a catalyst for the isophorone synthesis. M. G. Stevens (Chem. Commun. 3, 1999) achieves, with cesium-doped carbon nanotubes, an acetone conversion of 11.9% at an isophorone selectivity of 61%.

The synthesis of isophorone forms a whole series of unwanted by-products. These are, for example, diacetone alcohol, mesityl oxide, phorone, mesitylene and a series of higher condensation products (overcondensates) of acetone (e.g. xylitones and isoxylitones). For this reason, the achievement of high yields and selectivities for isophorone is difficult to attain.

PRIOR ART FOR II

The base-catalyzed reaction of hydrocyanic acid (HCN) with alpha,beta-unsaturated cyclic (or acyclic) ketones is a known reaction (Hydrocyanation of Conjugated Carbonyl Compounds, CHAPTER 3, Wataru Nagata and Mitsuru Yoshioka). Further processes are cited below.

PRIOR ART FOR III

The preparation of IPDA by aminating hydrogenation of IPN is known and has already been described many times.

In the simplest case (U.S. Pat. No. 3,352,913), IPN is reacted in the presence of hydrogen and of an excess of ammonia over a cobalt catalyst. First of all, IPN and ammonia form, through elimination of water, isophoronenitrileimine, IPNI, which is subsequently hydrogenated to IPDA.

containing organopolysiloxanes (EP 816 323), heteropolyacids (DE 44 26 472) and activated carbon (EP 061 137) as imination catalysts. As well as the reduction of the unwanted amino alcohol, other by-products are also distinctly suppressed, for example bicyclic compounds and those by-products which result from the elimination of HCN.

Particular reference is made to the problem of elimination of HCN from gamma-ketonitriles, such as IPN, in the literature (U.S. Pat. No. 3,352,913). Firstly, it is noted that HCN elimination reduces the yield of IPDA (EP 042 119, DE 44 26 472).

Secondly, it is pointed out that HCN acts as a catalyst poison and leads to deactivation of the hydrogenation catalyst (EP 394 967 A1, page 2 line 34 ff, page 3 line 44 ff). It is therefore recommended that the imination step be performed in such a way that a minimum amount of HCN is eliminated. The process is preferably to be run such that less than 0.001 mol of HCN is eliminated per mole of nitrile used (EP 394 967 page 5 line 49 ff). Based on the aminating hydrogenation of IPN, this is 163 ppmw (0.0163 percent by weight).

As well as the reduction in the cyanide concentration, there are descriptions of further methods of increasing the yield of IPDA in the aminating hydrogenation of IPN IPDA.

As already mentioned above, an excess of ammonia or the use of ammonia as a solvent has a positive effect on the yield (e.g. EP 449 089, EP 659 734, DE 12 29 078).

Modification with alkali metal hydroxides (EP 729 937) also leads to an increase in the IPDA yield. The fact that the addition of alkali metal hydroxides, particularly lithium hydroxide, in nitrile hydrogenations can increase the yield of primary amine is known from several publications (U.S. Pat. No. 4,375,003, EP 913 388). The catalysts can either be treated with alkali metal hydroxides before the reaction, or

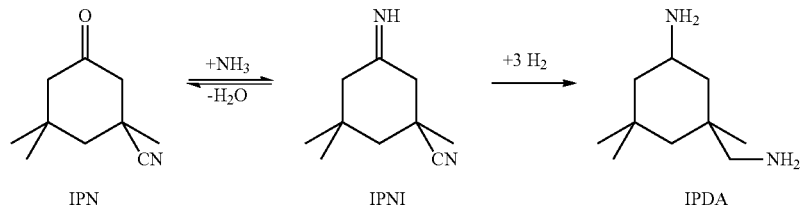

When the reaction is conducted in this way, the yield of IPDA is determined to a crucial degree by the excess of ammonia. The maximum IPDA yields achieved are about 80%. The main by-product is what is called the amino alcohol, IPAA, which results from the direct hydrogenation of the IPN.

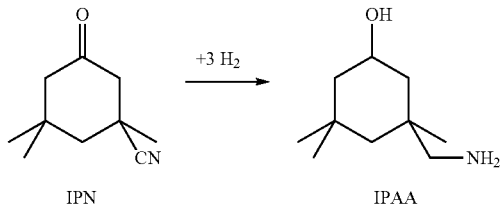

A significant rise in the IPDA yield is achieved when the formation of IPNI is accelerated by use of suitable imination catalysts. Suitable imination catalysts are, for example, acidic ion exchange resins (EP 042 119). In addition, it is also possible to use acidic metal oxides (EP 449 089), sulfo-else the alkali metal hydroxide is added to the reaction mixture during the reaction. Unless any great amounts of solvents such as ammonia, THF or methanol are used, the long-term stability of the LiOH-modified catalysts is quite good. In in-house experiments, however, we have found that, in the case of use of the abovementioned solvents, the LiOH is continuously washed off the catalyst, and thus the proportion of secondary amines rises again. In the case of a continuous process regime in which the solvent is removed from the mixture by distillation and recycled into the process, there is additionally deposition of the alkali metal hydroxides in the distillation columns. The columns have to be shut down and cleaned at regular intervals, and so the alkali modification leads indirectly to production shutdowns.

According to EP 913 387, selectivity can also be enhanced in the preparation of IPDA by using quaternary ammonium bases. Correspondingly modified catalysts, specifically in the case of use of a solvent, have a much longer service life than alkali-modified catalysts.

The problem addressed by this invention was, proceeding from acetone, to find an improved process for preparing 3-aminomethyl-3,5,5-trimethylcyclohexylamine.

The technical problem addressed by this invention was therefore to find a process which enables increased economic viability in the isophorone preparation. At the same time, ecological aspects should also be taken into account.

A further problem addressed by the present invention was that of finding a process for enhancing selectivity in the catalytic hydrogenation and/or the catalytic reductive amination of IPN to IPDA, which eliminates said disadvantages of the above-described processes.

It has been found that the reaction mixture which forms from step I. can be worked up by the inventive process in a particularly economically viable and ecologically favorable manner to give isophorone.

It has now likewise been found that, surprisingly, the problem can be solved by an increase in the cyanide ion concentration in the reaction mixture in step III., for example caused by the controlled elimination of HCN from IPN. This is surprising in that cyanide ions have been described as catalyst poisons and therefore, according to the prior art, a minimum concentration of cyanide ions is desirable for yield optimization and selectivity optimization. The increase in the cyanide ion concentration within a particular range surprisingly ensures a rise in selectivity for the same conversion in the hydrogenation of IPNI to IPDA.

The invention provides a process for preparing 3-aminomethyl-3,5,5-trimethylcyclohexylamine by
I. preparation of isophorone by catalyzed aldol condensations of acetone as a reactant, workup of the reaction product,
hydrolysis of the stream of value and separation into an organic fraction and an aqueous fraction,
recovery of isophorone from the organic fraction,
distillative workup of the aqueous fraction and passage of the vapors from the top of the distillative workup apparatus onward into the hydrolysis apparatus;
II. base-catalyzed reaction of isophorone with HCN to form isophoronenitrile;
III. preparation of isophoronediamine by means of catalytic hydrogenation and/or catalytic reductive amination of isophoronenitrile (IPN), in the presence of ammonia, hydrogen and at least one catalyst and optionally a solvent or solvent mixture, where the cyanide ion concentration in the reaction mixture which is sent to the hydrogenation is 200 ppmw to 5000 ppmw, based on the isophoronenitrile used.

I: Preparation of Isophorone

In the first step of the process according to the invention, in accordance with the invention, isophorone is prepared by catalyzed aldol condensations with acetone as the reactant. The details which follow accordingly relate to this step I.

According to the invention, in step I., the process for preparing isophorone by catalyzed aldol condensations with acetone as a reactant,
workup of the reaction product,
hydrolysis of the stream of value and separation into an organic fraction and an aqueous fraction,
recovery of isophorone from the organic fraction,
distillative workup of the aqueous fraction and passage of the vapors from the top of the distillative workup apparatus onward into the hydrolysis apparatus,
is performed.

The invention additionally provides, in step I., a process for preparing isophorone wherein the water from the bottoms of the distillative workup of the aqueous fraction is subjected to a flash evaporation and the purified water which forms is recycled into the process for preparing isophorone.

The inventive process in step I. can be performed continuously, batchwise or semicontinuously. However, it is preferably performed continuously.

Isophorone is prepared via catalyzed aldol condensations with acetone as the reactant. In the first step, two acetone molecules react via the diacetone alcohol intermediate with elimination of water to form mesityl oxide. In a further reaction the mesityl oxide reacts with a further acetone, again with elimination of water, to form isophorone.

Isophorone is thus the reaction product of a condensation of three molecules of acetone with the elimination of two molecules of water.

As a consequence of the chemical similarity of the reactant used (acetone) and the intermediates/products formed, the isophorone synthesis does not proceed particularly selectively. Due to the multitude of competing aldol condensation reactions, under reaction conditions, not only is the desired isophorone target molecule obtained, but also a whole series of unwanted (higher) condensation products (e.g. xylitones and isoxylitones), and also further secondary components (e.g. mesitylene).

The isophorone synthesis is thus characterized by a complex reaction network; the selectivity is highly dependent on the conversion. In order to minimize the formation of unwanted (higher) condensation products, the acetone conversion has to be limited. Particularly in the gas phase reaction, the catalyst used can be deactivated by coking residues which form.

It has been found that the reaction mixture which forms can be worked up by the inventive process in step I. in a particularly economically viable and ecologically favorable manner to give isophorone.

The condensation reaction of acetone to isophorone (reaction) is preferably performed in a catalyzed liquid phase reaction. Alternatively, isophorone can also be prepared by means of a gas phase reaction, or else by reaction in supercritical acetone.

For the performance of the reaction in step I. in accordance with the process according to the invention in the liquid phase, the acetone is converted to isophorone within the reactor used by catalytic reaction at temperatures in the range from 100 to 250° C., preferably 150-250° C. and more preferably 180-250° C., and a pressure range of 5 to 50 bar, preferably 10-50 bar and more preferably of 20-50 bar, it being possible to combine the values specified as desired.

For the performance of the reaction in step I. in accordance with the process according to the invention in the gas phase, the acetone is converted to isophorone within the reactor used by catalytic reaction at temperatures in the range from 100 to 400° C. and preferably 200-400° C.

For the performance of the reaction in step I. in accordance with the process according to the invention in the supercritical range, the acetone is converted to isophorone within the reactor used by catalytic reaction at temperatures in the range from 250 to 350° C. and a pressure range of 50 to 200 bar.

The catalytic reaction can be performed with the catalysts specified in the prior art, and the catalyst may be either a homogeneous or a heterogeneous catalyst. In the liquid phase, preference is given to using a homogeneous catalyst, and in the gas phase preference is given to using a heterogeneous catalyst. For the reaction in the supercritical range, it is possible to use either homogeneous or heterogeneous catalysts.

In the preferred reaction in the liquid phase, isophorone can be prepared by means of a homogeneous catalyst with amounts of alkali (NaOH or KOH) of <1% by weight, preferably of <0.5% by weight, more preferably <0.2% by weight. More preferably, the catalyst used is NaOH in amounts of 0.015 to 0.05% by weight. The water concentration used is determined by factors including the recycle streams of the workup processes; it should, based on the total amount of liquid, be <40%, preferably <30%.

The reaction can be performed in any desired reactors according to the prior art, for example tubular reactors, stirred tanks, stirred tank cascades, fixed bed reactors, pressure distillation reactors or reactive distillations, microstructured reactors, loop reactors, etc., or in combinations of any desired reactors. The choice of reactors is not restricted to the selection mentioned.

The term "pressure distillation reactor" should be equated here with apparatuses in which a reactive distillation is performed. Reactive distillation has been sufficiently well described in the specialist literature, for example in Ullmann's Encyclopedia of Industrial Chemistry (M. Sakuth, D. Reusch, R. Janowsky: Reactive Distillation © 2008 Wiley-VCH Verlag GmbH & Co KGaA, Weinheim, DOI: 10.1002/14356007.c22_c01.pub2). Here and in the literature cited, all standard processes and apparatuses for reactive distillation are described. If the term "reactive distillation column" is used in the following text of the patent specification, what is meant is all embodiments of reactive distillation as described in the literature.

In a preferred version, the reaction is conducted in reactive distillation columns, tubular reactors or fixed bed reactors. Particular preference is given to tubular reactors.

After performing the reaction, the reaction mixture is worked up and separated into the individual components. These are, as well as isophorone, what are called low boilers, for example acetone, diacetone alcohol and mesityl oxide, and also a series of higher condensation products (overcondensates) of acetone (e.g. xylitones and isoxylitones) and water, with or without catalyst. The separation is performed in full or in part.

The removal of the individual fractions can be performed by all separation methods, for example distillation, flash evaporation, crystallization, extraction, sorption, permeation, phase separation or combinations of the above, continuously or batchwise, in one or more stages. Preference is given to achieving separation by distillation in one or more apparatuses. The distillation can be performed spatially separately from the isophorone synthesis (reaction) or take place in one apparatus. Preferably, the individual fractions are removed by a reactive distillation, preferably in a reactive distillation column.

Particular preference is given to performing the removal spatially separately from the isophorone synthesis (reaction) in a reactive distillation column with a sidestream withdrawal.

Preferably, the removal is effected in three fractions:
a) A fraction composed of unconverted acetone, water and low boilers, for example diacetone alcohol and mesityl oxide, which is condensed and then recycled into the reactor for reaction.
b) A fraction in which colored substances in particular are enriched. This fraction is purified further and the materials of value present are recycled into the process.
c) A fraction composed particularly of isophorone, more highly condensed products and water, with or without catalyst, called stream of value. This fraction is subsequently subjected to a hydrolysis.

In the preferred embodiment, fraction a) is withdrawn as a vapor stream comprising essentially acetone, water and low boilers, essentially diacetone alcohol and mesityl oxide, condensed and added again to the reactor with the acetone, water and optionally catalyst feedstocks.

In the preferred embodiment, fraction b) is withdrawn as a sidestream of the distillation column, preferably of a reactive distillation column, optionally neutralized and worked up further. In the workup, it is possible to use all standard separation methods, for example distillation, flash evaporation, crystallization, extraction, sorption, permeation, phase separation, or combinations of the above. The purification can be performed continuously or batchwise, in one or more stages. The purification is preferably achieved by distillation. The purification is more preferably achieved by a combination of neutralization or extraction and subsequent distillation, preferably in a reactive distillation column. The worked-up phase is preferably conducted into the hydrolysis with the products of value composed of isophorone and high boilers, with or without catalyst. Any further phase obtained, composed of products of value essentially comprising acetone, diacetone alcohol and mesityl oxide, is preferably recycled into the reaction. Any residues obtained are sent to thermal utilization.

Fraction c) is subjected to a hydrolysis. The aim of the hydrolysis is to convert by-products partly or fully to isophorone, acetone and other products of value. The hydrolysis can be performed in all standard reactors, which have already been described above, or distillation columns or combinations of the two. Preference is given to performing the hydrolysis by a reactive distillation, in which the low boilers formed, essentially comprising acetone, diacetone alcohol and mesityl oxide, are removed directly from the hydrolysis zone and recycled into the reaction, and are thus no longer available for side reactions in the hydrolysis.

Most preferably, the hydrolysis of fraction c) is performed in an apparatus, by a reactive distillation, preferably in a reactive distillation column, with simultaneous separation of the reaction mixture into fractions a) to c), such that the products formed are correspondingly separated at the same time as fraction c) is hydrolyzed.

Optionally, the hydrolysis and the distillative removal can also take place in one apparatus with the isophorone synthesis (reaction).

The hydrolysis can be performed in all mixing ratios of the organic components with water, with or without catalyst. The water concentration in the hydrolysis is 0.1-99.9% by weight, preferably 30-90% by weight. In the case of homogeneous catalysis, the catalyst used in the hydrolysis is preferably that which is also used in the reaction section. Preference is given to catalyst concentrations of 0.001-10% by weight, more preferably of 0.05-1% by weight. The pressure in the hydrolysis reactor is 1-200 bar, preferably 20-60 bar; more preferably, the hydrolysis is performed at least at the pressure which also exists in the isophorone synthesis step (reaction). The hydrolysis temperature is 100-300° C., preferably 210-260° C. More preferably in the case of use of a reactive distillation column, a temperature or temperature profile will be established according to the boiling temperatures in the bottoms and at the individual separation or reaction stages.

The hydrolysis can be performed in one or more apparatuses, in one stage or multiple stages.

The fraction c) thus worked up is subsequently removed from the hydrolysis reactor or reactive distillation column, cooled and subjected to a phase separation.

The phase separation is effected to give an essentially organic fraction d) and an essentially aqueous fraction e), which, in the case of homogeneous catalysis, also comprises the catalyst. It is possible to use customary phase separation vessels with and without internals. The phase separation is effected at a temperature between 0-200° C., preferably at 0-100° C. and more preferably at 20-70° C., and a pressure of 1-150 bar and preferably 20-60 bar, more preferably at the pressure which also exists in the hydrolysis.

The essentially organic fraction d), comprising the isophorone target product, is optionally neutralized and purified by customary methods, so as to obtain an isophorone with the desired purity and color stability. It is possible here to use all standard separation methods, for example distillation, flash evaporation, crystallization, extraction, sorption, permeation, phase separation or combinations of the above. The purification can be performed continuously or batchwise, in one or more stages, under pressure or under reduced pressure. The purification is preferably achieved by distillation. The purification is more preferably achieved by a combination of neutralization or extraction and subsequent distillation.

At this point, the distillative workup of the aqueous fraction e) (wastewater cleaning) and conduction of the vapors from the top of the distillative workup apparatus into the hydrolysis apparatus will be described in detail.

The essentially aqueous fraction e) is supplied to a wastewater cleaning operation. This involves the separation of the water of reaction as the main constituent, with or without the catalyst, from any undissolved organic components, for example isophorone, acetone and more highly condensed products. The wastewater cleaning operation is preferably performed in one or more distillation columns. It is essential to the invention that the vapors of the wastewater column are passed directly into the apparatus in which the hydrolysis takes place. This simultaneously solves several problems with the current prior art:

1) Since the vapors consist essentially of water, a necessary sufficiently high water concentration is established in the hydrolysis section, such that no additional fresh water need be introduced into the hydrolysis.
2) The organic components dissolved in fraction e) are recycled partially or completely into the process via the vapors of the wastewater column. This minimizes organic contamination in the wastewater and, since the contamination is essentially isophorone, increases the overall yield in the process. This novel connection of the wastewater column thus makes a significant contribution to the ecological and economic process regime.
3) Moreover, the necessary heat for the hydrolysis or the distillative separation of the reaction mixture is provided by the vapors; no separate heating is required.

The pressure in the wastewater column is 1-200 bar, preferably 20-60 bar. Particular preference is given to working at the system pressure which is established in the overall hydrolysis/wastewater column system when the vapors of the wastewater column are passed directly into the hydrolysis section of the reactive distillation. The temperature in the wastewater column corresponds to the boiling temperature of fraction e) under the pressure conditions. The preferred temperature of the vapors is 200-300° C.

There follows a detailed description of how the water from the bottoms of the distillative workup of the aqueous fraction is subjected to a flash evaporation and the cleaned water formed is recycled into the process for preparation of isophorone.

The wastewater obtained in the bottom of the wastewater column (stream f) can be cooled and discarded. Preferably, the wastewater f), however, is sent to a flash evaporation and thus separated further. The vapors g) of the flash evaporation stage, which consist essentially of pure water, can be condensed and recycled as water into the process, preferably into the reaction, for example for dilution of the catalyst used (in the case of homogeneous catalysis). This once again reduces the amount of wastewater. The flash evaporation can be performed in one or more stages, continuously or batchwise. The pressure in the flash evaporation is in any case below the pressure in the wastewater column. In the process according to the invention, preference is given to the use of a flash evaporation.

All distillation and reaction steps in the process can be performed in reactors or apparatuses with or without internals, for example dephlegmators, unordered internals or random packagings, ordered internals or structured packings, trays with or without forced flow.

All metallic materials which are in contact with the product and are used for the reaction, and the apparatuses produced from the metallic materials and the internals thereof, must be stable to alkalis. Depending on the risk, different stability requirements may exist. For the stabilities, not only the chemical and/or mechanical properties are of significance, but also the methods of manufacture employed and the assessment standards during the testing.

For the metallic materials, reference is made in some cases to the AD 2000-Merkblatt HP 0, 11.2008 edition (General Principles of Design, Manufacture and Associated Tests) and DIN EN 10020, 07.2000 edition (Determination and Classification of Grades of Steel). The material groups named therein are cited to specify the designations (e.g. "austenitic stainless steel"). If meaningful in a technical sense, the statements apply to all industrially available variants of the materials (for example forged variants, rolled variants and cast variants) with comparable stability to alkali corrosion.

a) For pressure-bearing components in contact with product, any materials suitable according to the prior art can be employed, for example:
  Heat-resistant steels (e.g. material subgroups 5.1 to 5.4 and 6.1 to 6.4 according to AD 2000 HP 0)
  Austenitic stainless steels (e.g. material subgroups 8.1 to 8.2 according to AD 2000 HP 0)
  Ferrite-free austenitic stainless steels (e.g. material subgroups 8.1 to 8.2 according to AD 2000 HP 0)
  Ferritic-austenitic stainless steels (e.g. material subgroups 10.1 to 10.2 according to AD 2000 HP 0)
  Nickel and nickel alloys (e.g. material subgroups 41 to 46 according to AD 2000 HP 0)

It is also possible to employ combinations of the abovementioned materials. In this case, the choice of materials is not restricted to the selection mentioned and also includes equivalent or higher-quality variants in terms of corrosion. Preference is given to materials which, according to the prior art, taking account of the stress conditions and risks, feature industrial stability to alkalis. It is not possible to dispense with heat treatments if this impermissibly alters the technical stability to alkalis.

b) For non-pressure-bearing components in contact with product, any materials suitable according to the prior art can be employed, for example:
  All materials mentioned under a)
  Unalloyed steels (e.g. material subgroups 1.1 to 1.2 according to AD 2000 HP 0)
  Unalloyed steels and other alloyed steels (e.g. according to DIN EN 10020)

It is also possible to employ combinations of the abovementioned materials. In this case, the choice of materials is not restricted to the selection mentioned and also includes equivalent or higher-quality variants in terms of corrosion. Preference is given to materials which, according to the prior art, taking account of the stress conditions and risks, feature sufficient stability to alkalis. For non-pressure-bearing components, it may be possible to accept temporary stabilities depending on the risk. It is not possible to dispense with heat treatments if this impermissibly alters the technical stability to alkalis.

c) The material properties are altered by suitable manufacturing processes which are described hereinafter according to the designations given in DIN 8580, 09.2003 edition (Manufacturing Processes—Terms and Definitions, Division). The following manufacturing processes can be employed, for example, for the processing of the metallic materials:

Primary shaping (e.g. casting)
Reshaping (e.g. cold forming and hot forming)
Separating (e.g. machining with geometrically defined blade and machining with geometrically undefined blade)
Joining (e.g. fusion welding)
Coating (e.g. coating from the liquid state, melt dipping, plating, thermal spraying, sintering, electrocoating, chemical coating and coating from the gaseous and vaporous state)
Manufacturing processes which alter material properties (consolidation by forming, for example forging, rolling, blasting; heat treatment, for example tempering, recrystallization annealing, low-voltage annealing, normalization annealing; thermomechanical treatments, for example the combination of heat treatment and forming treatment; sintering and firing).

It is also possible to employ combinations of the abovementioned manufacturing processes. In this case, the choice of manufacturing processes is not restricted to the selection mentioned. Preference is given to processes which, according to the prior art, ensure the required alkali stability of the respective materials and apparatuses.

d) The following tests on apparatuses and internals, and more particularly on the weld bonds thereof, for example, can be employed:

Magnet particle testing MT
Penetration testing PT
Radiographic testing RT
Ultrasound testing UT
Visual testing VT
Hardness testing HT
Alloy analysis Combinations of the abovementioned test methods are also possible. In this case, the choice of test methods is not restricted to the selection mentioned. Preference is given to test methods and assessment principles which, according to the prior art, contribute to ensuring the required alkali stability of the respective components.

II: Preparation of Isophoronenitrile

In the second step of the process according to the invention, the isophorone prepared in accordance with the invention is reacted with HCN to form isophoronenitrile (IPN, 3-cyano-3,5,5-trimethylcyclohexanone). The details which follow accordingly relate to this step II.

The base-catalyzed reaction of hydrocyanic acid (HCN) with alpha,beta-unsaturated cyclic (or acyclic) ketones is a known reaction (Hydrocyanation of Conjugated Carbonyl Compounds, CHAPTER 3, Wataru Nagata and Mitsuru Yoshioka).

The reaction of isophorone with HCN to give IPN can be described by the following reaction equation:

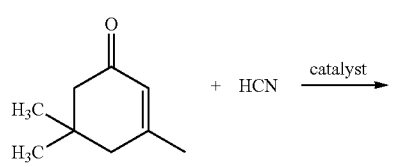

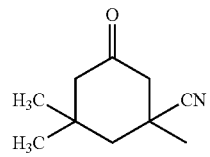

The catalysts for the preparation of the beta-cyano ketones, for example IPN, are generally bases which provide free cyanide ions for the 1,4-addition reaction. The reaction with HCN can be performed either in solution or without solvent.

Suitable catalysts are basic alkali metal or alkaline earth metal compounds, onium compounds, organic bases, or specific processes using phase transfer catalysts. The different catalyst systems are illustrated in detail hereinafter:

a) Catalysts for Preparation of Isophoronenitrile from Isophorone and Hydrocyanic Acid, Consisting of Basic Alkali Metal or Alkaline Earth Metal Compounds:

Corresponding examples for preparation of cyano ketones by reaction of unsaturated ketones of basic compounds with hydrocyanic acid over an alkaline catalyst which forms cyanide ions are described in DE 1085871. Suitable catalysts mentioned are alkali metals and their carbonates; and also alkaline earth metals and alkali metal and alkaline earth metal alkoxides, oxides, hydroxides, peroxides and cyanides; tertiary amines and quarternary ammonium bases. The catalyst is required in an amount of 0.1 to 20% by weight, based on the total weight of the reaction participants. The conversion is preferably effected at temperatures of 150 to 225° C. and at standard pressure.

DE 1240521 describes processes for preparing gamma-ketocarbonitriles from alpha,beta-unsaturated ketones. The preparation is effected by using high hydrocyanic acid concentrations and heterogeneous catalysts (alkaline catalysts on supports, for example clay fragments) without solvent. Basic catalysts mentioned are, for example, oxides, hydroxides, cyanides and alkoxides of the alkali metals and alkaline earth metals. It is essential that the catalysts have solid supports. Synthesis is effected at temperatures between 50 and 350° C.

Analogous processes are known from DE 1240854.

EP 0433615 describes the use of lithium hydroxide (LiOH) as a catalyst; according to EP 0558332, lithium cyanide which has been prepared beforehand from LiOH can also be used as a catalyst.

In addition, EP01418172 describes the use of a calcium oxide having a surface area of >1.5 m²/g. The reaction preferably takes place at temperatures between 150-170° C.

a) Catalysts for Preparation of Isophoronenitrile from Isophorone and Hydrocyanic Acid, Consisting of Onium Compounds or the Specific Use Thereof:

JP 61033157 describes the preparation of isophoronenitrile by reaction of hydrocyanic acid and isophorone in the presence of quaternary ammonium or phosphonium hydroxides as catalysts.

According to EP 558799, reaction of isophorone with HCN can also be accomplished using onium cyanides, for example tetraalkylammonium cyanide or tributylsulfonium cyanide, as a catalyst.

EP 0671384 relates to the use of quaternary ammonium salts with hydrogencarbonate or alkylcarbonate counterions.

The use of quaternary ammonium or phosphonium salts, for example ammonium or phosphonium cyanides, is also described in U.S. Pat. No. 5,183,915 or EP 0502707, using a basic cocatalyst (potassium carbonate or sodium carbonate) in the latter case.

The document U.S. Pat. No. 5,011,968 describes the preparation of IPN by reaction of isophorone with HCN and tetramethylammonium hydroxide as a catalyst and subsequent thermal destruction of the catalyst to give trimethylamine and removal with the offgas.

c) Catalysts for Preparation of Isophoronenitrile from Isophorone and Hydrocyanic Acid, by Means of Phase Transfer Catalysis or Using a Biphasic Reaction System:

EP 28179 describes the preparation of IPN from IP (organic phase) and cyanides (aqueous phase) in a biphasic system with a phase transfer medium used in catalytic amounts. The phase transfer catalysts used are quaternary ammonium and phosphonium salts (for example tetraethylammonium bromide or disodium phosphate), which are soluble in the organic phase.

According to U.S. Pat. No. 4,299,775, the catalyst used may be sodium or potassium cyanide in the presence of water and an inert solvent, and also of an onium phase transfer catalyst.

EP 0425806 (DE 69009394T2) describes the reaction of isophorone with alkaline cyanides in stoichiometric amounts in homogeneous solution with an aqueous and organic solvent mixture, with simultaneous and gradual neutralization with inorganic acids. The phases separate again during the reaction and can be separated from one another in this way.

d) Catalysts for Preparation of Isophoronenitrile from Isophorone and Hydrocyanic Acid, by Means of Particular Organic Bases:

EP0985659 (equivalent to DE19836474) describes the use of 1,3-dimethylimidazolium-4-carboxylate as a catalyst.

Diazobicycloalkenes are likewise suitable as catalysts for the preparation of IPN by reaction of hydrocyanic acid and isophorone (JP 61033158).

In JP04253948, isophorone is converted to IPN with HCN in the presence of guanidine (0.01-0.5 mol based on 1 mol of isophorone) as a base.

e) Catalysts for Preparation of Isophoronenitrile from Isophorone and Hydrocyanic Acid, by Means of Use of Particular Solvents:

In JP57116038, isophorone is converted to IPN with HCN in the presence of a basic catalyst and a glycol (for example ethylene glycol).

JP04164057 describes the preparation of IPN by equimolar reaction of IP with HCN under base catalysis in 1,3-dimethyl-2-imidazolidinone as a solvent.

JP04112862 includes the preparation of IPN by reaction of isophorone with HCN, alkaline catalysts and DMSO (dimethyl sulfoxide) and/or DMF (dimethylformamide) as solvents.

Of the abovementioned catalysts, preference is given to using those from the group of the basic alkali metal or alkaline earth metal compounds in the process step of the invention.

According to the invention, the conversion can be performed either homogeneously or under heterogeneous base catalysis. In the case of homogeneous catalysis, catalyst and reactants are present in the same phase. A typical example is a metal salt dissolved in a solvent (for example 25% by weight sodium methoxide solution, dissolved in methanol), in which the reactants react.

In heterogeneous catalysis, catalyst and reactants are present in different phases. Usually, a solid catalyst (e.g. metal oxide) is exposed to reactants present in the liquid phase, i.e. when there is a phase boundary between the catalyst and the reaction mixture. The catalyst is generally a solid, while the reactants are gaseous and/or liquid. In the case of heterogeneously catalyzed process operations, the crucial processes take place at the surface of the solid.

Generally, both homogeneous and heterogeneous base catalysis are suitable in the process step of the invention. More particularly, the catalysts are alkali metals and their carbonates; and also alkaline earth metals and alkali metal and alkaline earth metal alkoxides, oxides, hydroxides, peroxides and cyanides.

In the process step of the invention, preference is given to using homogeneous base catalysis. For this purpose, very particular preference is given to using alkali metal alkoxides, especially sodium methoxide, as catalysts.

The hydrocyanic acid used can be used in pure form or else as a mixture with stabilizers. Suitable stabilizers are all compounds known to those skilled in the art for this purpose, for example phosphoric acid, sulfur dioxide and oxalic acid.

Preference is given to using phosphoric acid, sulfur dioxide or mixtures thereof as stabilizers for the hydrocyanic acid. The proportion of stabilizers is typically in the range from 0.1 to 2% by weight, based on the hydrocyanic acid used, preferably in the range from 0.5 to 1% by weight.

The conversion can be undertaken in the presence or absence of inert solvents. Particular preference is given to using isophorone in a molar excess, based on the hydrocyanic acid used, and to not adding any external solvent.

Generally, the process according to the invention is performed in such a way that an excess of isophorone is used, since a higher selectivity for isophoronenitrile is thus achieved. In general, the molar isophorone/HCN ratio is >1:1, generally 19:1 to 1.5:1, preferably 3:1 to 1.5:1.

The catalyst concentration, based on the amount of isophorone used, is in the range from 0.03 to 20% by weight, preferably in the range from 0.03 to 1% by weight.

The entire amount of the isophorone can be initially charged and brought to the desired reaction temperature, before the HCN is added in the presence of the catalyst.

The HCN is preferably metered in such a way that a homogeneous distribution of the reactants (isophorone and HCN) is ensured. The metered addition of HCN is accomplished in a customary manner known to those skilled in the art, for example by means of static mixers, pumps or atomization.

The reaction temperatures are typically in the range from 130 to 225° C., preferably in the range from 135 to 195° C. and most preferably in the range from 140 to 175° C.

The reaction is performed at pressures of 0.01 to 10 bar, preferably 1 to 5 bar, more preferably at standard pressure (atmospheric pressure).

Within the above-detailed reaction parameters, the HCN is metered in so as to result in a sufficiently low concentration of HCN, and a high selectivity and a high conversion to isophoronenitrile can thus be achieved. The selectivity with respect to IPN should be >95%, preferably >98%, more preferably >99%.

In the course of this, only a low level of polymerization of the HCN may occur, since this would adversely affect the conversion and selectivity.

Preferably, the concentrations of unconverted, free HCN and the total concentration of cyanide ions (sum of free HCN and cyanide bound in the form of cyanohydrins of isophorone and isophoronenitrile) are determined and the reaction conditions are adjusted so as to obtain an optimized selectivity with respect to IPN. Said cyanide ion concentrations are preferably determined by titration.

The process according to the invention, in a preferred manner, can be performed continuously, discontinuously or semi-continuously, especially continuously.

In a preferred embodiment, the reaction procedure, according to the catalyst used, is performed in a stirred tank, a stirred tank cascade, a circulation reactor, a flow tube, one or more fixed bed reactors or a column.

The workup of the reaction mixture after the reaction has ended is accomplished in a customary manner known to those skilled in the art.

According to JP 06065182, after performance of the reaction of HCN with IP, the alkaline catalyst can be neutralized and the reaction mixture worked up directly in the distillation.

Alternatively, according to JP 06065183, the alkaline reaction mixture can be mixed with an inert solvent and worked up in a thin-film evaporator. This removes the catalyst, the high boilers and the solvent. The resulting isophoronenitrile is then purified in a further column.

The catalyst can be removed, for example, by the processes described in DE 1085871 or EP 0433615.

Preferably, excess isophorone is removed by distillation and advantageously reused. For this purpose, the isophorone removed is mixed with fresh isophorone and recycled into the reaction reactor. The isophoronenitrile formed is separated from possible secondary components by distillative workup.

III: Preparation of 3-aminomethyl-3,5,5-trimethylcyclohexylamine

In the third step of the process according to the invention, the isophoronenitrile prepared in accordance with the invention is converted by means of catalytic hydrogenation and/or catalytic reductive amination to isophoronediamine. The details which follow accordingly relate to this step III.

The invention provides, according to step III., a process for preparing isophoronediamine by means of catalytic hydrogenation and/or catalytic reductive amination of isophoronenitrile (IPN), in the presence of ammonia, hydrogen and at least one catalyst and optionally a solvent or solvent mixture, where the cyanide ion concentration in the reaction mixture which is sent to the hydrogenation is 200 ppmw to 5000 ppmw, based on the isophoronenitrile used.

The setting of the cyanide ion concentration of 200 ppmw to 5000 ppmw, preferably to 3000, can be achieved by various measures, for example by controlled metered addition of HCN or cyanide salts such as KCN, or else by the use of suitable IPN qualities. In the process according to the invention, the setting of the cyanide ion concentration is preferably achieved by causing controlled redissociation of the IPN in the imination stage. Contrary to the teaching of EP 394 967 A1, this can in accordance with the invention by an increase in the temperature in the imination stage by 5-50 K, preferably 7-30 K, more preferably 10-20 K, above the temperature which, depending on the use of an imination catalyst, is needed to achieve a conversion of IPN to IPNI of at least 80% in the imination stage.

It is possible to perform the process according to the invention as per step III. in one stage or in a plurality of stages.

If the process is performed in one stage, isophoronenitrile is subjected to aminating hydrogenation directly in the presence of ammonia, hydrogen, a hydrogenation catalyst and possibly further additions, and in the presence or absence of organic solvents.

The expression "in a plurality of stages" means that isophoronenitrile is first converted fully or partly in a separate reactor or reactor section to isophoronenitrileimine, and this isophoronenitrileimine is subjected to aminating hydrogenation as a pure substance or in a mixture with other components, in the presence of at least ammonia.

A preferred embodiment of the process according to the invention for preparing IPDA as per step III. is a two-stage process: In the first stage, at least some of the IPN used, in the presence or absence of an imination catalyst and/or of solvents, is converted by reaction with ammonia to isophoronenitrileimine. The conversion of IPN to IPNI after the imination should be greater than 80%, preferably greater than 90%, more preferably greater than 95%. In the second stage, the first stage reaction product, as obtained or after a further treatment and/or addition of further ammonia, is subjected to aminating hydrogenation over hydrogenation catalysts in the presence of at least ammonia and hydrogen and in the presence or absence of an organic solvent at a temperature of 20 to 150° C., preferably 40 to 130° C., and a pressure of 0.3 to 50 MPa, preferably 5 to 30 MPa.

In a further preferred embodiment of step III., the conversion of IPN to IPDA is effected in three separate reaction spaces. In the first reaction space, IPN is converted to isophoronenitrileimine with excess ammonia over imination catalysts at temperatures between 20 and 150° C. and pressures between 5 and 30 MPa. In the second reaction space, the reaction products formed are hydrogenated with hydrogen in the presence of excess ammonia over hydrogenation catalysts at temperatures between 20 and 130° C. and pressures of 5 to 30 MPa. In the third reaction space, the reaction products formed are hydrogenated over the catalysts for use in accordance with the invention at temperatures between 100 and 160° C. and pressures of 5 to 30 MPa.

In order to accelerate the establishment of equilibrium in the imination reaction, it is appropriate to use an imination catalyst. For this purpose, the imination catalysts known according to the prior art can be used. Suitable catalysts are, for example, inorganic or organic ion exchangers (see EP 042 119), supported heteropolyacids (see DE 44 26 472), acidic metal oxides, especially aluminum oxide and titanium dioxide (see EP 449 089), organopolysiloxanes containing sulfo groups (DE 196 27 265.3), and acidic zeolites and activated carbon (EP 061 137). In the case of use of an imination catalyst, the reaction temperature may be between 10 and 150° C., preferably between 30 and 130° C. and most preferably between 40 and 100° C. The pressure is between the autogenous pressure of the mixture and 50 MPa. Preference is given to performing the imination reaction at the pressure at which the subsequent reductive amination is also performed.

Even though the imination of isophoronenitrile with liquid ammonia is preferably performed without addition of further solvents, it is also possible to work in the presence of additional solvents. Suitable solvents are monohydric alcohols having 1 to 4 carbon atoms, especially methanol, and ethers, particularly THF, MTBE and dioxane.

In the imination stage, between 1 and 500 mol, preferably 5 and 200 mol, more preferably between 5 and 100 mol, of ammonia are used per mole of IPN used. Typical catalyst hourly space velocities are in the range from 0.01 to 10 kg of IPN per kg of catalyst and hour, preferably 0.5 to 10 and more preferably 0.5 to 5 kg of IPN per kg of catalyst and hour.

In the case of imination in the presence of an imination catalyst, the catalyst may be present in the form of a suspension catalyst or fixed bed catalyst. It is advantageous to use fixed bed catalysts. In a particularly preferred embodiment, IPN and ammonia are passed continuously from the bottom upward through a reaction tube filled with imination catalyst.

The hydrogenation is typically effected at temperatures between 20 and 150° C., preferably 40 and 130° C., and pressures of 0.3 to 50 MPa, preferably 5 to 30 MPa. It is also possible to perform the hydrogenation in the presence of the solvents already mentioned for the imination stage. The main advantage in the case of use of a solvent is that the hydrogenation can be performed at lower pressures between 0.3 and 10 MPa.

The hydrogen required for the hydrogenation can be supplied to the reactor either in excess, for example at up to 10

000 molar equivalents, or only in such an amount that the hydrogen consumed by reaction and the portion of the hydrogen which leaves the reactor dissolved in the product stream is replenished. In the case of a continuous mode of operation, the hydrogen can be supplied in cocurrent or countercurrent.

In a preferred embodiment, the hydrogenation is effected in liquid ammonia as solvent. Between 1 and 500 mol, preferably 5 and 200 mol, more preferably between 5 and 100 mol, of ammonia are used per mole of IPN. It is appropriate to use at least the amount of ammonia which has been established in the upstream imination. However, the ammonia content can also be increased to the desired value before the hydrogenation by addition of additional ammonia.

The catalysts used may in principle be any catalysts which catalyze the hydrogenation of nitrile and/or imine groups with hydrogen. Particularly suitable catalysts are nickel, copper, iron, palladium, rhodium, ruthenium and cobalt catalysts, very particularly ruthenium and cobalt catalysts. To increase the activity, selectivity and/or service life, the catalysts may additionally comprise doping metals or other modifiers. Typical doping metals are, for example, Mo, Fe, Ag, Cr, Ni, V, Ga, In, Bi, Ti, Zr and Mn, and the rare earths. Typical modifiers are, for example, those with which the acid-base properties of the catalysts can be influenced, preferably alkali metals and alkaline earth metals or compounds thereof, preferably magnesium and calcium compounds, and also phosphoric acid or sulfuric acid and compounds thereof.

The catalysts can be used in the form of powders or shaped bodies, for example extrudates or compressed powders. It is possible to employ unsupported catalysts, Raney-type catalysts or supported catalysts. Preference is given to Raney-type and supported catalysts. Suitable support materials are, for example, silicon dioxide, aluminum oxide, aluminosilicates, titanium dioxide, zirconium dioxide, kieselguhr, aluminum-silicon mixed oxides, magnesium oxide and activated carbon. The active metal can be applied to the support material in a manner known to those skilled in the art, for example by impregnation, spray application or precipitation. According to the method of catalyst production, further preparation steps known to those skilled in the art are necessary, for example drying, calcination, shaping and activation. For shaping, it is optionally possible to add further assistants, for example graphite or magnesium stearate. The required volume of the hydrogenation catalysts to be used is guided by the LHSV (liquid hourly space velocity), which is dependent on the operating pressure, the temperature, the concentration and the catalyst activity and has to be observed in order to ensure maximum completeness of hydrogenation of the IPN used. Typically, the LHSV in the case of use of the mixture of IPN, ammonia and hydrogen, the use of which is preferred, is between 0.5 and 4 liters of IPN/ammonia mixture per liter of catalyst and hour, preferably between 1 and 3 $l_{sol} l_{cat}^{-1} h^{-1}$.

It is preferable that the hydrogenation catalysts for use are first conditioned with ammonia before they are used in the hydrogenation. For this purpose, the catalysts are contacted with ammonia or with mixtures of ammonia and one or more solvents. The conditioning preferably follows installation of the catalysts in the hydrogenation reactor, but it can also precede the installation of the catalysts. For conditioning, between 0.2 and 3, preferably 0.5 and 2, m³ of ammonia per m³ of catalyst and hour are used. It is customary to work at temperatures between 20 and 150° C., preferably 40 to 130° C. Particular preference is given to running through a temperature ramp in which the catalyst, beginning at moderately elevated temperature, preferably between 20 and 50° C., is heated gradually up to the reaction temperature desired at a later stage for the hydrogenation, preferably 20 to 150° C. The conditioning is preferably performed in the presence of hydrogen, the partial pressure of the hydrogen used in the reactor covering the range from 0.1 to 50 MPa, preferably 5 to 40 MPa, more preferably 10 to 30 MPa. The duration of the conditioning, depending on the amount of ammonia used, is preferably between 1 and 48 h, more preferably between 12 and 24 h.

In the preferred two-stage process, the mixture comprising isophoronenitrileimine is hydrogenated with the aid of a shaped hydrogenation catalyst in the second stage. The mixture supplied to the hydrogenation stage may directly be any which is obtained in the imination of IPN with ammonia in the first stage, or as obtained after addition or removal of components, for example ammonia, organic solvents, bases, cocatalysts, cyanide salts, hydrocyanic acid and/or water. Preference is given to performing the hydrogenation continuously in fixed bed reactors which can be operated in trickle mode or liquid phase mode. Suitable reactor types are, for example, shaft furnaces, tray reactors or shell and tube reactors. It is also possible to connect a plurality of fixed bed reactors in series for the hydrogenation, in which case each of the reactors is operated either in trickle bed mode or liquid phase mode.

Apart from the aforementioned constituents of the mixture to be supplied to the imination stage, this may additionally comprise higher- or lower-boiling fractions than IPDA from the distillative workup of the reaction mixture drawn off from the trickle bed reactor. Such fractions may, apart from residues of IPDA, also comprise those by-products from which IPDA forms again under reaction conditions. It is particularly advantageous to recycle the higher-boiling fraction than IPDA, which, apart from residues of IPDA, comprises 2-aza-4,6,6-trimethylbicyclo[3.2.1]octane as the main product. It is likewise particularly advantageous to recycle incompletely converted IPN, especially fractions comprising isophoroneaminonitrile. The recycled material can also, if desired, be added directly to the reaction mixture to be supplied to the hydrogenation stage.

In the hydrogenation of IPN or isophoronenitrileimine, it is possible to form two different stereoisomers. Through the choice of a temperature profile in the hydrogenation step, it is possible to influence the isomer ratio. It is possible, for example, first to partly hydrogenate a mixture comprising IPN or isophoronenitrileimine at a temperature between 20 and 90° C., and then to complete the reaction in a second step within a temperature range between 90 and 150° C. The observation of relatively low reaction temperatures in the 1st step can shift the selectivity in favor of the cis isomer. The observation of relatively low reaction temperatures at the start of the reaction additionally has the advantage that the thermally labile isophoronenitrileimine is hydrogenated under particularly gentle conditions, and side reactions are suppressed as a result. Isophoroneaminonitrile, which is formed as an intermediate, is much more thermally stable and can therefore be hydrogenated at higher temperatures without any risk of further side reactions. The unwanted side reactions also include the elimination of HCN. In the process according to the invention, a certain cyanide ion concentration has a positive effect on the selectivity of the hydrogenation stage. This effect becomes increasingly apparent when the cyanide ions are present from the start in the hydrogenation stage and not just formed during the hydrogenation. Therefore, elimination of HCN during the hydrogenation stage should be avoided.

The desired temperature profile can be implemented, for example, by the series connection of two or more separately heatable reactors. It is also possible to implement a rising temperature profile in only one hydrogenation reactor. Particular preference is given to performing the hydrogenation reaction in an adiabatic trickle bed reactor, in which the reaction mixture is supplied to the reactor at temperatures between 20 and 90° C., and owing to the heat of reaction which occurs and is absorbed by the reaction mixture leaves it again between 90 and 150° C.

The reaction mixture leaving the hydrogenation is purified further by the customary methods, in order to obtain an IPDA with the desired quality. It is possible here to use all standard separation methods, for example distillation, flash evaporation, crystallization, extraction, sorption, permeation, phase separation or combinations of the above. The purification can be performed continuously, batchwise, in one or more stages, under reduced pressure or under pressure. Possible components which are removed, for example, in the further purification are hydrogen, ammonia, water, and by-products obtained in the preparation of IPDA from IPN, for example the IPDA is obtained at the top of a column. The low- and high-boiling impurities and water are preferably removed under a reduced pressure between 100 Pa and 0.0999 MPa and bottom temperatures of 50-300° C. All secondary components can be sent to thermal utilization.

The present invention according to step III. is thus particularly characterized in that, contrary to the prior art to date, the selectivity of the reductive amination of IPN to IPDA is not maximized through the explicit minimization of the cyanide ion concentration. Instead, a minimum concentration of 200 ppmw based on the mass of IPN used is beneficial for the selectivity of the hydrogenation of the IPNI to IPDA. More particularly, the formation of the bicyclic compound 2-aza-4,6,6-trimethylbicyclo[3.2.1]octane, a main by-product in the reductive amination of IPN to IPDA, which is formed by the intramolecular nucleophilic attack of the amine group of IPAN on the carbon atom of the nitrile group, is significantly reduced.

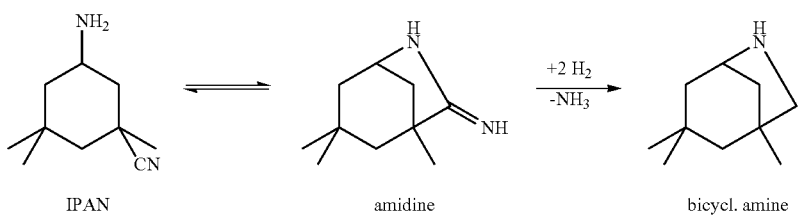

hydrogenated HCN elimination products or impurities in the IPN, methylated by-products and/or incompletely hydrogenated intermediates.

Preferably, the purification is achieved by distillation under pressure and/or under reduced pressure in a plurality of steps. For this purpose, it is possible to use any desired distillation columns with or without internals, for example dephlegmators, dividing walls, unordered internals or random packings, ordered internals or structured packings, or trays with or without forced flow.

In a first step, especially hydrogen, inert gases, ammonia, low-boiling impurities and possibly also water are removed fully or partly in one or more distillation columns. The removal is preferably effected at a pressure lower than in the reaction step. If the removal is effected in a plurality of distillation steps, it is advantageous to lower the pressure stepwise. Most preferably, the removal is effected above 1 bar and with bottom temperatures of 0-200° C. The use of a stripping gas for removal of low-boiling impurities may be advantageous. Especially ammonia and hydrogen and proportions of the low-boiling impurities can be recycled fully or partly into the process (reaction). The low-boiling impurities and possibly proportions of hydrogen and ammonia are sent to thermal utilization.

In a second step, low-boiling impurities, water and high-boiling impurities are fully or partly removed. This can be effected in one or more distillation columns. This may involve distilling water off together with organic, low-boiling impurities and possibly proportions of IPDA via the top of the column and, after condensation, separating them into an aqueous phase and an organic phase. In this case, the organic phase can be recycled partly as reflux into the column. If the second step of the distillation is performed in a single column (for example a dividing wall column), the IPDA is withdrawn via a sidestream with the desired purity, while the high-boiling impurities are obtained in the bottom of the column. If the separation, however, is performed in two or more stages, Examples III, 1 and 2 show two comparable experimental settings which differ solely by the cyanide ion concentration in the feed. It becomes clear that the metered addition of an amount of cyanide corresponding to 1000 ppmw of HCN reduces the amount of bicyclic amine formed from 4.13% to 2.03%. The amidine intermediate is lowered from 1.40% to 1.00%. Since no reduced activity was detected (conversion of IPN and IPAN constant), the yield of IPDA in the crude product rises from 93.23% to 95.69%.

As well as the positive influence on the selectivity, however, the cyanide ions also have the parallel poisoning effect, described in the literature, on hydrogenation catalysts. Therefore, an excessive increase in the cyanide ion concentration is not productive, since the deactivating action otherwise becomes dominant. Preference is given to a concentration based on the IPN used of not more than 3000 ppmw. A distinctly higher cyanide concentration of 5000 ppmw based on the IPN used still ensures reduced by-product concentrations (bicyclic amine 2.36%, amidine 1.03%), but the proportion of unconverted IPAN rises from 0.63% to 1.15%, as a result of which the overall yield of IPDA at 94.62% falls by one percentage point. This is illustrated in Example 3 for III.

EXAMPLES

For I

Example

Inventive

A crude isophorone mixture consisting of isophorone, lower-boiling components, higher-boiling components, and also water and catalyst, which has been obtained by one of the procedures described above, is withdrawn from the hydrolysis apparatus, cooled to about 40-60° C. and subjected to a phase separation. The phase ratio is 1 part organic phase, 4 parts aqueous phase. In the aqueous phase, 1% by weight of isophorone is accordingly still present, corresponding to about 4% by weight of the organic phase. In the subsequent wastewater distillation, almost all of the isophorone content and 75% by weight of the water are vaporized and passed into the hydrolysis apparatus.

In the course of cooling of the bottoms from the wastewater column, a further 25% by weight of the water is recovered by flash evaporation.

Calculation for 1 tonne of isophorone production: 4% by weight (about 40 kg) of extra isophorone production, minimization of the volume of wastewater, low organic contamination of the wastewater.

Comparison, Noninventive:

Comparison with the conventional process: about 4% by weight of isophorone lost via the wastewater, based on 1 tonne of isophorone production. The extra demand for water corresponds to 5 times the volume, based on 1 tonne of isophorone production. The volume of wastewater is likewise 5 times higher, based on 1 tonne of isophorone production.

For II

General Details

The experiments concerning formation of isophoronenitrile from isophorone and hydrocyanic acid were performed isothermally and discontinuously or semicontinuously in a stirred tank apparatus with dropping funnel and reflux condenser. A standard experiment was performed by initially charging the reactor with the main amount of isophorone and a portion of the hydrocyanic acid (stabilized with 0.5-1.0% phosphoric acid) and bringing them to the desired reaction temperature. The hydrocyanic acid was added in a mixture with isophorone via a dropping funnel. The time t=0 was fixed by the addition of the catalyst. Shortly before the addition of the catalyst, the composition of the reaction mixture was determined by sampling and gas chromatography analysis, in order to take account of possible changes during the heating phase. After addition of the catalyst, the residual amount of hydrocyanic acid/isophorone was continuously added dropwise. The metered addition of the hydrocyanic acid must not be too fast, since the result is otherwise polymerization of the hydrocyanic acid through the cyanide ions formed. This forms a brown polymeric solid, which has to be removed. The samples were taken at given times with a syringe. The samples were weighed and analyzed (determination of the cyanide content by titration and GC determination). These determinations of the reaction mixture can be effected by processes known to those skilled in the art. Preferably, the excess isophorone is removed by a distillation and fed back to the process. The workup of the reaction mixture after the reaction has ended is accomplished in a customary manner known to those skilled in the art. Preferably, excess isophorone is removed by distillation and advantageously reused. Thereafter, the isophoronenitrile formed is separated from secondary components, preferably likewise by distillation.

Gas Chromatography Determination of the Reaction Products:

Instrument: HP3/Agilent GC 6890
Separation column: HP-5 Agilent (19091J-433) 30 m×250 μm×0.25 μm nominal
Const. flow: 0.9 ml/min
Injector: Temperature: 200° C.
Total flow: 84.6 ml/min
Split flow: 81.1 ml/min (1:94.8)
Detector: Temperature: 250° C.
$H_2$ flow: 40 ml/min
Air flow: 450 ml/min
Make-up flow ($N_2$): 45 ml/min
Oven: Temperature program: 90° C./3 min at 5° C./min to 150° C. at 10° C./min to 300° C./29 min
Sample preparation: 1000 mg sample+70 mg of C-12 as ISTD in 10 ml of toluene
Injection volume: 1.0 μL
Evaluation: ISTD %

TABLE 1

| | Compound class | | | |
|---|---|---|---|---|
| | Alkoxide | Alkoxide | Onium compound | Alkoxide |
| Catalyst | LiOMe | KOMe | $(CH_3)_4NOH*(5H_2O)$ | NaOMe |
| Temperature [° C.] | 150 | 150 | 150 | 150 |
| HCN conversion [%] | 98 | 92.8 | 95 | 98.5 |
| Yield (IPN in %) | 45 | 40 | 40 | 45.9 |
| Selectivity (IPN in %) | 95.3 | 98.9 | 93 | 99 |
| Reaction time [min] | 345 | 266 | 84 | 305 |

Conclusion: NaOMe as a homogeneous catalyst at 150° C. shows good performance in terms of yield and selectivity.

TABLE 2

| | Compound class | | | |
|---|---|---|---|---|
| | Hydroxide | Alkoxide | Oxide | Carbonate |
| Catalyst | NaOH | KOMe | MgO | $Na_2CO_3$ |
| Temperature [° C.] | 170 | 170 | 170 | 170 |
| HCN conversion [%] | 76 | 96.3 | 24 | 82 |
| Yield (IPN in %) | 31 | 43 | 1 | 42 |
| Selectivity (IPN in %) | 98 | 98.6 | 67.4 | 92 |
| Reaction time [min] | 262 | 262 | 248 | 202 |

| | Compound class | | | |
|---|---|---|---|---|
| | Carbonate | Carbonate | Carbonate | Cyanide |
| Catalyst | $Li_2CO_3$ | $K_2CO_3$ | $CaCO_3$ | NaCN |
| Temperature [° C.] | 170 | 170 | 170 | 170 |
| HCN conversion [%] | 17 | 94.9 | 0.2 | 82 |
| Yield (IPN in %) | 0.6 | 42 | 0.02 | 17 |
| Selectivity (IPN in %) | 66.9 | 99 | 5.6 | 98 |
| Reaction time [min] | 103 | 120 | 102 | 129 |

Conclusion: A wide variety of basic (slurry) catalysts showed very good performance at T=170° C.

For III

In examples 1-3, the cyanide was added manually. This ensures comparable conditions among the results. However, preference is given in accordance with the invention to the production of the cyanide ions in the prereactor.

Description of the Continuous Experimental Apparatus:

IPN and ammonia are mixed continuously in a vessel. From there, the mixture passes through a pump into the 2 l prereactor, which is filled with ion exchanger according to EP 042 119 for catalysis of imine formation from IPN and ammonia. Subsequently, the mixture is hydrogenated in a 6 l trickle bed reactor with three individually heatable temperature zones. After the reaction, the ammonia is removed and recycled into the process; in addition, consumed ammonia is replaced continuously.

Example 1

In the above-described experimental apparatus, a 21.5% ammoniacal IPN solution was subjected to aminating hydrogenation at an LHSV of 1.8 $l_{sol} l_{cat}^{-1} h^{-1}$. The catalyst used was a cobalt catalyst supported on kieselguhr. The pressure in the plant was 252 bar. The temperature profile established in the hydrogenation corresponds to an adiabatic reaction regime; the temperature at the reactor inlet was 70° C., and at the outlet 115° C. The mixture leaving the reaction section was analyzed by gas chromatography. The composition is shown in table 1.

TABLE 1

| Substance | Proportion by GC |
|---|---|
| IPDA | 93.23 |
| IPN | 0.00 |
| IPAN | 0.71 |
| TMCA | 0.11 |
| bicycl. amine | 4.13 |
| amidine | 1.40 |
| Sum of other unknown by-products | 0.28 |
| Sum of unknowns | 0.14 |

Example 2

As example 1, except that 40 g/h of a 10% aqueous KCN solution were additionally metered in downstream of the imination reactor. This corresponds to a space velocity of 1000 ppmw of HCN based on IPN. The results of the gas chromatography analysis of the reaction product are shown in table 2:

TABLE 2

| Substance | Proportion by GC |
|---|---|
| IPDA | 95.69 |
| IPN | 0.00 |
| IPAN | 0.63 |
| TMCA | 0.09 |
| bicycl. amine | 2.03 |
| amidine | 1.00 |
| Sum of other unknown by-products | 0.42 |
| Sum of unknowns | 0.14 |

Example 3

As example 1, except that 100 g/h of a 20% aqueous KCN solution were additionally metered in downstream of the imination reactor. This corresponds to a space velocity of 5000 ppmw of HCN based on IPN. The results of the gas chromatography analysis of the reaction product are shown in table 3:

TABLE 3

| Substance | Proportion by GC |
|---|---|
| IPDA | 94.62 |
| IPN | 0.00 |
| IPAN | 1.15 |
| TMCA | 0.24 |
| bicycl. amine | 2.36 |
| amidine | 1.03 |
| Sum of other unknown by-products | 0.47 |
| Sum of unknowns | 0.13 |

The invention claimed is:

1. A process for preparing isophoronediamine, the process comprising:
   (i) reacting acetone via a catalyzed aldol condensation in a reactor, thereby obtaining a reaction product comprising isophorone,
   (ii) working-up the reaction product comprising isophorone, thereby obtaining a stream of value,
   (iii) hydrolyzing the stream of value in a hydrolysis apparatus,
   (iv) separating the stream of value into an organic fraction and an aqueous fraction,
   (v) recovering isophorone from the organic fraction,
   (vi) distilling the aqueous fraction in a distillative workup apparatus comprising a top and a bottom,
   (vii) passing vapors from the top of the distillative workup apparatus onward into the hydrolysis apparatus,
   (viii) subjecting water from the bottom of the distillative workup apparatus to a flash evaporation, thereby obtaining purified water which is recycled into the reactor for preparing isophorone,
   (ix) reacting isophorone with HCN via a base-catalyzed reaction, thereby obtaining isophoronenitrile,
   (x) reacting isophoronenitrile with ammonia optionally in the presence of at least one of an imination catalyst and a solvent to obtain a first product comprising isophoronenitrileimine with a conversion of isophoronenitrile to isophoronenitrileimine of greater than 80%, and
   (xi) subjecting a reaction mixture comprising the first product as obtained from said reacting (x) or after a further treatment to aminating hydrogenation over a hydrogenation catalyst in the presence of ammonia, hydrogen, and optionally an organic solvent at a temperature of from 20 to 150° C. and a pressure of from 0.3 to 50 MPa, thereby obtaining a second product comprising isophoronediamine,
   wherein a cyanide ion concentration in the reaction mixture subjected to the aminating hydrogenation is of from 200 ppmw to 5000 ppmw, based on the isophoronenitrile used.

2. The process of claim 1, wherein said reacting (i) is performed in a liquid phase at a temperature of from 100 to 250° C., and a pressure of from 5 to 50 bar.

3. The process of claim 1, wherein said reacting (i) is performed in a gas phase at a temperature of from 100 to 400° C.

4. The process of claim 1, wherein said reacting (i) is performed in a supercritical range at a temperature of from 250 to 350° C. and a pressure of from 50 to 200 bar.

5. The process of claim 1, wherein a homogeneous or a heterogeneous catalyst is used in said reacting (i).

6. The process of claim 1, wherein said reacting (i) is effected in a liquid phase with a homogeneous catalyst.

7. The process of claim 6, wherein the homogeneous catalyst is alkali of <1% by weight.

8. The process of claim 1, wherein said reacting (i) is performed in at least one reactor selected from the group consisting of a tubular reactor, a stirred tank, a stirred tank cascade, a fixed bed reactor, a reactive distillation column, a microstructured reactor, and a loop reactor.

9. The process of claim 1, wherein said reacting (i) is performed in a reactive distillation column, a tubular reactor or a fixed bed reactor.

10. The process of claim 1, wherein said working-up (ii) comprises (xii) separating the reaction product comprising isophorone into individual components and removing the individual components in full or in part.

11. The process of claim 10, wherein the individual components are removed by at least one separation method selected from the group consisting of distillation, flash evaporation, crystallization, extraction, sorption, permeation, and phase separation, continuously or batchwise, in one or more stages.

12. The process of claim 1, wherein said distilling (vi) is performed spatially separately from said reacting (i) or takes place in a reaction apparatus.

13. The process of claim 10, wherein the individual components are removed via a reactive distillation spatially separately from said reacting (i).

14. The process of claim 10, wherein the individual components are removed in three fractions:
   a) a fraction comprising unconverted acetone, water and low boilers, wherein the fraction a) is condensed and then recycled into the reactor;
   b) a fraction comprising enriched colored substances, wherein the fraction b) is purified further and materials of value are recycled into the reactor; and
   c) a fraction comprising isophorone, more highly condensed products, water, and catalyst, wherein the fraction c) is subsequently subjected to a hydrolysis.

15. The process of claim 14, wherein the fraction a) is withdrawn as a vapor stream comprising acetone, water and low boilers comprising diacetone alcohol and mesityl oxide, condensed and added again to the reactor with a feed stock comprising acetone, water, and catalyst.

16. The process of claim 14, wherein the fraction b) is withdrawn as a sidestream of a distillation column.

17. The process of claim 14, wherein the fraction b) is purified by a combination of neutralization or extraction and subsequent distillation in a reactive distillation column, thereby obtaining a worked-up phase.

18. The process of claim 17, wherein the worked-up phase of the fraction b) is conducted into the hydrolysis apparatus with products of value comprising isophorone and high boilers, with or without catalyst.

19. The process of claim 17, wherein any further phase of the fraction b) comprises acetone, diacetone alcohol and mesityl oxide, and is recycled into the reactor.

20. The process of claim 14, wherein the fraction c) is subjected to the hydrolysis in which by-products are converted partly or fully to isophorone, acetone and other products of value.

21. The process of claim 1, wherein said hydrolyzing (iii) is performed in a reactive distillation column in which low boilers comprising acetone, diacetone alcohol and mesityl oxide, are obtained and recycled into the reactor.

22. The process of claim 14, wherein the hydrolysis of the fraction c) is performed in an apparatus via a reactive distillation with a simultaneous separation of the reaction product into the fractions a), b), and c).

23. The process of claim 14, wherein the hydrolysis of the fraction c) is effected at a water concentration of 0.1-99.9% by weight.

24. The process of claim 14, wherein the hydrolysis of the fraction c) is effected at a catalyst concentration of 0.001-10% by weight.

25. The process of claim 14, wherein the hydrolysis of the fraction c) is performed at a pressure of 1-200 bar.

26. The process of claim 14, wherein the hydrolysis of the fraction c) is effected at a temperature of 100-300° C.

27. The process of claim 14, wherein the hydrolysis of the fraction c) is performed in a reactive distillation column at a temperature or a temperature profile established according to boiling temperatures in bottoms and at individual separation or reaction stages.

28. The process of claim 14, wherein the fraction c) is separated into an organic fraction d) and an aqueous fraction e).

29. The process of claim 28, wherein the organic fraction d) is purified by distillation.

30. The process of claim 28, wherein the aqueous fraction e) is sent to a wastewater cleaning operation which optionally is performed in one or more distillation columns.

31. The process of claim 30, wherein the wastewater cleaning operation is performed at a pressure of 1-200 bar.

32. The process of claim 30, wherein the wastewater cleaning operation is performed at a system pressure established in an overall hydrolysis/wastewater column system.

33. The process of claim 30, wherein a pressure in the flash evaporation is below a pressure in the wastewater column.

34. The process of claim 33, wherein vapors g) obtained from the flash evaporation consist essentially of pure water and are condensed and recycled as water into the reactor.

35. The process of claim 1, wherein a basic alkali metal or alkaline earth metal compound, an onium compound, or an organic base is used as catalyst in said reacting (ix).

36. The process of claim 1, wherein a basic alkali metal or alkaline earth metal compound is used as catalyst in said reacting (ix).

37. The process of claim 35, wherein the basic alkali metal or alkaline earth metal is selected from the group consisting of an oxide, a hydroxide, a cyanide, and an alkoxide.

38. The process of claim 1, wherein a molar ratio of isophorone/HCN in said reacting (ix) is from 19:1 to 1.5:1.

39. The process of claim 1, wherein a catalyst concentration in said reacting (ix), based on the isophorone used, is of from 0.03 to 20% by weight.

40. The process of claim 1, wherein said reacting (ix) occurs at a temperature of from 130 to 225° C.

41. The process of claim 1, wherein said reacting (ix) is performed in a stirred tank, a stirred tank cascade, a circulation reactor, a flow tube, one or more fixed bed reactors or a column.

42. The process of claim 1, wherein excess isophorone is removed in said reacting (ix) by distillation and the isophorone removed is mixed with fresh isophorone and recycled into said reacting (ix).

43. The process of claim 1, wherein the cyanide ion concentration in the reaction mixture subjected to the aminating hydrogenation is of from 200 ppmw to 3000 ppmw.

44. The process of claim 1, wherein the cyanide ion concentration is adjusted by controlled metered addition of HCN or cyanide salts, or by use of isophoronenitrile qualities having a cyanide ion concentration of from 200 ppmw to 5000 ppmw.

45. The process of claim 1, wherein the cyanide ion concentration is adjusted by controlled redissociation of isophoronenitrile in said reacting (x).

46. The process of claim 45, wherein the controlled redissociation of isophoronenitrile occurs at an increased temperature by 5-50 K above a temperature which, depending on the imination catalyst used, is needed to achieve a conversion of isophoronenitrile to isophoronenitrileimine of at least 80% in said reacting (x).

47. The process of claim 1, wherein isophoronenitrile is converted to isophoronediamine in three separate reaction spaces:
   in a first reaction space, isophoronenitrile is converted to isophoronenitrileimine with excess ammonia over the imination catalyst at a temperature of from 20 to 150° C. and a pressure of from 5 to 30 MPa, thereby obtaining a first reaction product;

in a second reaction space, the first reaction product is hydrogenated with hydrogen in the presence of excess ammonia over a first hydrogenation catalyst at a temperature of from 20 to 130° C. and a pressure of from 5 to 30 MPa, thereby obtaining a second reaction product; and in a third reaction space, the second reaction product is hydrogenated over a second hydrogenation catalyst at a temperature of from 100 to 160° C. and a pressure of from 5 to 30 MPa.

48. The process of claim 1, wherein said reacting (x) is effected in the presence of at least one imination catalyst.

49. The process of claim 1, wherein liquid ammonia is used in said reacting (x), which occurs without additional solvent.

50. The process of claim 49, wherein an amount of from 1 and 500 mol of the liquid ammonia is used per mole of isophoronenitrile.

51. The process of claim 49, wherein said reacting (x) occurs in the presence of a suspension catalyst or a fixed bed catalyst.

52. The process of claim 1, wherein isophoronenitrile and ammonia in said reacting (x) are conducted continuously from a bottom upward through a reaction tube filled with the imination catalyst.

53. The process of claim 1, wherein in said subjecting (xi), hydrogen is supplied either in excess or in such an amount that hydrogen consumed during said subjecting (xi) and dissolved in the second product is replenished.

54. The process of claim 1, wherein said subjecting (xi) is performed in liquid ammonia as a solvent in an amount of from 1 to 500 mol per mole of isophoronenitrile.

55. The process of claim 1, wherein the hydrogenation catalyst used in said subjecting (xi) is nickel, copper, iron, palladium, rhodium, ruthenium or cobalt.

56. The process of claim 1, wherein the hydrogenation catalyst in said subjecting (xi) further comprises a doping metal.

57. The process of claim 1, wherein the hydrogenation catalyst in said subjecting (xi) further comprises a modifier.

58. The process of claim 1, wherein the hydrogenation catalyst used in said subjecting (xi) is a powder or a shaped body.

59. The process of claim 1, wherein the hydrogenation catalyst in said subjecting (xi) is an unsupported catalyst, a Raney-type catalyst, or a supported catalyst.

60. The process of claim 59, wherein a support material for the supported catalyst is selected from the group consisting of silicon dioxide, aluminum oxide, aluminosilicates, titanium dioxide, zirconium dioxide, kieselguhr, an aluminum-silicon mixed oxide, magnesium oxide and activated carbon.

61. The process of claim 1, wherein the hydrogenation catalyst used in said subjecting (xi) is first conditioned with ammonia before the hydrogenation catalyst is used.

62. The process of claim 1, wherein the reaction mixture is hydrogenated in said subjecting (xi) in the presence of a shaped hydrogenation catalyst.

63. The process of claim 1, wherein said subjecting (xi) is performed continuously in a fixed bed reactor operated in a trickle mode or a liquid phase mode.

64. The process of claim 1, further comprising:
(xiii) purifying the second product in one or more stages, thereby obtaining isophoronediamine.

65. The process of claim 64, wherein
said purifying (xiii) occurs in two stages,
in a first stage, hydrogen, inert gases, ammonia, low-boiling impurities and optionally water are completely or partially removed in one or more distillation columns, and
in a second stage, further low-boiling impurities, water and high-boiling impurities are completely or partially removed in the one or more distillation columns.

* * * * *